United States Patent
Remaut et al.

(10) Patent No.: US 9,974,719 B2
(45) Date of Patent: May 22, 2018

(54) SOLID COSMETIC MAKEUP AND/OR CARE COMPOSITION

(75) Inventors: Geoffroy Remaut, Fresnes (FR); Magali Ravaud, Paris (FR)

(73) Assignee: L'OREAL, Paris (FR)

( * ) Notice: Subject to any disclaimer, the term of this patent is extended or adjusted under 35 U.S.C. 154(b) by 41 days.

(21) Appl. No.: 14/114,534

(22) PCT Filed: Apr. 26, 2012

(86) PCT No.: PCT/IB2012/052087
§ 371 (c)(1),
(2), (4) Date: Oct. 29, 2013

(87) PCT Pub. No.: WO2012/147042
PCT Pub. Date: Nov. 1, 2012

(65) Prior Publication Data
US 2014/0065084 A1    Mar. 6, 2014

Related U.S. Application Data

(60) Provisional application No. 61/486,803, filed on May 17, 2011.

(30) Foreign Application Priority Data

Apr. 29, 2011  (FR) ..................................... 11 53686

(51) Int. Cl.
| | | |
|---|---|---|
| A61K 8/06 | (2006.01) | |
| A61K 8/34 | (2006.01) | |
| A61K 8/37 | (2006.01) | |
| A61K 8/81 | (2006.01) | |
| A61Q 1/02 | (2006.01) | |
| A61Q 9/00 | (2006.01) | |
| A61Q 17/04 | (2006.01) | |
| A61Q 19/00 | (2006.01) | |
| A61Q 19/08 | (2006.01) | |

(52) U.S. Cl.
CPC ................ *A61K 8/062* (2013.01); *A61K 8/06* (2013.01); *A61K 8/342* (2013.01); *A61K 8/37* (2013.01); *A61K 8/375* (2013.01); *A61K 8/8147* (2013.01); *A61Q 1/02* (2013.01); *A61Q 9/00* (2013.01); *A61Q 17/04* (2013.01); *A61Q 19/00* (2013.01); *A61Q 19/08* (2013.01); *A61K 2800/10* (2013.01); *A61Q 19/005* (2013.01); *A61Q 19/007* (2013.01)

(58) Field of Classification Search
CPC .......... A61K 8/06; A61K 8/062; A61K 8/342; A61K 8/37; A61K 8/375; A61K 8/8147; A61K 2800/10; A61Q 1/02; A61Q 9/00; A61Q 17/04; A61Q 19/00; A61Q 19/08; A61Q 19/005; A61Q 19/007
USPC ......................................... 424/59, 63, 78.03
See application file for complete search history.

(56) References Cited

U.S. PATENT DOCUMENTS

| | | |
|---|---|---|
| 4,776,976 A | 10/1988 | Nakamura et al. |
| 5,849,280 A | 12/1998 | Rechelbacher et al. |
| 6,090,375 A | 7/2000 | Rechelbacher et al. |
| 6,096,325 A * | 8/2000 | Date et al. .................... 424/401 |
| 6,312,676 B1 | 11/2001 | Rechelbacher et al. |
| 6,558,680 B1 | 5/2003 | Riedel et al. |
| 7,074,419 B2 | 7/2006 | Dietz et al. |
| 2003/0170281 A1 | 9/2003 | Riedel et al. |
| 2003/0235539 A1* | 12/2003 | Mongiat et al. ................ 424/59 |
| 2004/0142009 A1* | 7/2004 | Ansmann .................. A61K 8/31 424/401 |
| 2005/0112153 A1* | 5/2005 | Wagoner ................ A61K 8/922 424/401 |

FOREIGN PATENT DOCUMENTS

| | | |
|---|---|---|
| CN | 1897911 A | 1/2007 |
| DE | 195 16 702 | 11/1996 |
| DE | 20 2004 012 807 | 11/2004 |
| EP | 1 541 152 | 6/2005 |
| WO | WO 2005/058269 A1 | 6/2005 |

OTHER PUBLICATIONS

Buchanan et al., Hydrogels: Crosslinked Poly(Sodium Acrylate) Hydrogels, Polymer Bulletin (1986) 15:325-332 (8 pages).*
International Search Report dated Oct. 22, 2012 in PCT/IB12/052087 Filed Apr. 26, 2012, 3 pages.
Second Office Action dated Jul. 23, 2015 in Chinese Patent Application No. 201280030063.0 with English translation.

* cited by examiner

*Primary Examiner* — Ernst V Arnold
*Assistant Examiner* — Miriam A Levin
(74) *Attorney, Agent, or Firm* — Oblon, McClelland, Maier & Neustadt, L.L.P.

(57) ABSTRACT

The present invention relates to a cosmetic composition for making up and/or caring for keratin materials, in the form of an oil-in-water solid emulsion, comprising, in a physiologically acceptable medium: —from 4.0% to 8.0% by weight, relative to the total weight of the composition, of at least one fatty alcohol, —from 1.0% to 3.0% by weight, relative to the total weight of the composition, of at least one solid linear ester, —from 2.5% to 6.0% by weight, relative to the total weight of the composition, of at least one non-ethoxylated glyceryl stearate, and —from 0.25% to 0.50% by weight, relative to the total weight of the composition, of sodium polyacrylate.

15 Claims, No Drawings

SOLID COSMETIC MAKEUP AND/OR CARE COMPOSITION

The present invention relates to the field of caring for and/or making up keratin materials, and more particularly to the field of solid cast products.

In the cosmetics field, the search for novel products and novel textures is continuous.

Users are in search of compositions that give a novel sensory experience, especially in terms of the "feel" during the uptake of the product and the application to keratin materials.

Cast cosmetic products are particularly appreciated, on account of their ease of use, the infinite number of forms that they can adopt, and their stability associated with their solid nature.

To obtain these products, it has already been recommended to favour the use of vegetable butters in these compositions. Unfortunately, the use of such compounds does not prove satisfactory insofar as they give the composition a greasy and tacky nature that users do not appreciate.

Consequently, there remains a need for cast makeup and/or care compositions that are free of the defects mentioned above.

Surprisingly, it has been shown that a particularly advantageous texture can be obtained with the compositions according to the present invention obtained by mixing in precise amounts at least one fatty alcohol, at least one solid linear ester, at least one non-ethoxylated glyceryl stearate and sodium polyacrylate.

Thus, according to a first of its aspects, the present invention is directed towards a cosmetic composition for making up and/or caring for keratin materials, in the form of an oil-in-water solid emulsion, comprising, in a physiologically acceptable medium:
- from 4.0% to 8.0% by weight, relative to the total weight of the composition, of at least one fatty alcohol,
- from 1.0% to 3.0% by weight, relative to the total weight of the composition, of at least one solid linear ester,
- from 2.5% to 6.0% by weight, relative to the total weight of the composition, of at least one non-ethoxylated glyceryl stearate, and
- from 0.25% to 0.50% by weight, relative to the total weight of the composition, of sodium polyacrylate.

According to one preferred embodiment, the composition is in the form of a cast product.

The composition according to the invention is especially a composition intended to be applied to keratin materials, in particular the skin and more particularly facial skin.

The compositions that are more particularly under consideration according to the invention are solid and are in the form of cast products, obtained by hot-casting in a mould, especially a jar, and cooling to room temperature via a phenomenon of setting to a solid or via a cooling tunnel according to the industrially available tools, which are well known to those skilled in the art.

Their texture is thick and is comparable to that of a butter.

The compositions according to the invention in the form of a cast product are endowed with satisfactory properties in terms of non-greasy and non-tacky effect, and they are such that they give the user a very satisfactory sensory experience, in terms of feel, softness and glidance.

It has been observed that the deposit of the composition according to the invention on keratin materials, in particular the skin, has no undesirable greasy and tacky feel.

In addition, a composition according to the invention gives the user, when he takes it up and uses it on keratin materials, in particular the skin, a pleasant sensory experience.

In particular, a composition according to the invention proves to be easy for the user to take up, spreads easily on keratin materials, in particular the skin, and is moreover entirely satisfactory in terms of cosmetic properties, comfort and moisturization.

These compositions are also characterized by easy industrial implementation.

Finally, by virtue of its cast nature, such a composition also has the advantage of satisfying a consumer expectation in terms of cosmetic products that are "nomad" in the sense that they can be easily stored and transported under all conditions.

The composition according to the invention may be a skin makeup and/or care composition, and may constitute a face powder, an eyeshadow, a lipstick, a face product, a foundation, a concealer product, a body makeup product, a facial or body care product, an antisun product or a haircare product, especially a hair mask.

More especially, but not exclusively, the invention relates to a facial or body care product.

More especially, but not exclusively, the invention relates to a foundation composition. In this case, it will comprise at least one dyestuff and/or pigment.

According to one preferred embodiment, the present invention relates to a cosmetic composition as defined above, which is especially useful for preventing and/or treating sensitive and/or dry skin.

According to a second aspect, the present invention is directed towards protecting a process for preparing the composition, comprising at least the following steps:
- the preparation of a fatty phase comprising a mixture of 4.0% to 8.0% by weight of at least one fatty alcohol, 1.0% to 3.0% by weight of at least one solid linear ester, 2.5% to 6.0% by weight of at least one non-ethoxylated glyceryl stearate, relative to the total weight of the composition, and optionally an oil,
- the addition of the fatty phase to an aqueous phase at a minimum temperature of 65° C.,
- reduction of the temperature of the mixture to a temperature of between 60 and 65° C. and preferably between 62 and 63° C.,
- the addition of 0.25% to 0.50% by weight, relative to the total weight of the composition, of sodium polyacrylate,
- maintenance of stirring, preferably with a turbomixer, down to the crystallization temperature of the mixture,
- pouring of the composition into a conditioning jar at this same crystallization temperature, and
- preferably, leaving the conditioned composition to stand preferably for one month at room temperature.

According to yet another of its aspects, the present invention relates to a cosmetic composition for making up and/or caring for keratin materials, characterized in that it may be obtained via the process defined above.

According to one preferred mode, a composition according to the invention is in the form of a foundation composition.

According to a third subject, the present invention is directed towards a cosmetic process for making up and/or caring for keratin materials, comprising the application to the said keratin materials of a composition as defined previously, especially for the purposes of moisturizing the skin and more particularly dry skin.

DEFINITIONS

The term "solid" characterizes the state of the composition at room temperature (25° C.) and at atmospheric pressure (760 mmHg), i.e. a composition of high consistency, which retains its form during storage. As opposed to "fluid" compositions, it does not flow under its own weight.

The term "physiologically acceptable medium" is intended to denote a medium that is particularly suitable for applying a composition of the invention to keratin materials, especially the skin and more particularly to facial skin.

The physiologically acceptable medium is generally adapted to the nature of the support onto which the composition is to be applied, and also to the form in which the composition is to be packaged.

For the purposes of the present invention, the term "keratin materials" is intended to cover the skin, mucous membranes such as the lips, the nails and keratin fibres, such as the eyelashes and the hair. The skin and the lips, in particular facial skin, are most particularly considered according to the invention.

Oil-in-Water Solid Emulsion

The composition according to the invention is an oil-in-water solid emulsion.

Such a composition is advantageously in the form of a cast product, obtained by hot-casting in a mould, especially a jar, and cooling to room temperature via a phenomenon of setting to a solid or via a cooling tunnel according to the industrially available tools, which are well known to those skilled in the art.

The cohesion therein is thus ensured by solidification of at least one of its constituents during the implementation.

More particularly, a composition according to the invention may be prepared according to the process comprising at least the following steps:

the preparation of a fatty phase comprising a mixture of 4.0% to 8.0% by weight of at least one fatty alcohol, 1.0% to 3.0% by weight of at least one solid linear ester, 2.5% to 6.0% by weight of at least one non-ethoxylated glyceryl stearate, relative to the total weight of the composition, and optionally an oil, the addition of the fatty phase to an aqueous phase at a minimum temperature of 65° C., reduction of the temperature of the mixture to a temperature of between 60 and 65° C. and preferably between 62 and 63° C., the addition of 0.25% to 0.50% by weight, relative to the total weight of the composition, of sodium polyacrylate, maintenance of stirring, preferably with a turbomixer, down to the crystallization temperature of the mixture, pouring of the composition into a conditioning jar at this same crystallization temperature, and preferably, leaving the conditioned composition to stand for one month at room temperature.

The composition according to the invention may advantageously have a crystallization temperature ranging from 38 to 60° C., in particular from 38 to 45° C., in particular measured by DSC with a liberated energy ranging from −0.2 to 1 W/g. The value of this crystallization temperature is modifiable to within ±3° C.

This characterization by differential scanning calorimetry (DSC) may be performed with a DSC Q100 V9.4 BUILD 287 machine. The measurement is performed in temperature ramps from −20° C. to 120° C., over 3 melting cycles with a heating rate of 10° C./minute and crystallization ramps from 120 to −20° C. with a cooling rate of 10° C./minute for the first two cycles, and a cooling rate of 5° C./minute for the third cycle, with 6 mg of sample of the composition to be characterized.

Over the third cycle, the variation of the difference in power absorbed by the empty crucible and by the crucible containing the sample is measured as a function of the temperature. The crystallization temperature is the temperature value corresponding to the top of the peak of the curve representing the variation in the difference in power absorbed as a function of the temperature.

The texture of the composition may be characterized by viscosity measurements.

Protocol for Measuring the Viscosity:

The viscosity measurement is generally performed at 20° C., using a Rheomat RM180 viscometer equipped with a No. 4 spindle, the measurement being performed after 10 minutes of rotation of the spindle in the composition (after which time stabilization of the viscosity and of the spin speed of the spindle are observed), at a shear rate of 200 $s^{-1}$.

The composition according to the invention advantageously has a thick texture on "setting", and its viscosity at t=0 is more particularly greater than 95 poises after a few days of casting and up to 220 poises after several months.

Thus, advantageously, a composition according to the invention may have, at a temperature of 20° C., a viscosity of between 95 and 220 poises at t=0, between 65 and 200 at t=30 seconds and between 30 and 150 at t=10 minutes.

The texture of the composition may also advantageously be characterized by a hardness, when it is subjected to a penetration test with a cylindrical module.

For the purposes of the present invention, the term "hardness" is understood to mean the maximum penetration force obtained during the operation described below and expressed in grams.

It is measured at 20° C. using a texturometer sold under the name TAXT2i or TA XTPlus by the company Rheo, equipped with a cylindrical spindle, by measuring the change in force (compressive force or penetration force) (F) as a function of time.

A sample of the composition to be characterized is introduced into a crucible with a thickness at least equal to 20 mm and a surface area at least equal to 15 $cm^2$.

The sample is thermostatically maintained at 20° C. Nine measurements are taken for a same composition, either at different locations evenly distributed and spaced out over the sample, or on different samples for a same composition. The average of these nine measurements indicates the hardness of the composition with a 95% confidence interval.

Thus, advantageously, a composition according to the invention may have, at a temperature of 20° C. when it is measured using the texturometer sold under the name TA XTPlus by the company Rheo, a hardness of greater than or equal to 100 g better still greater than or equal to 160 g or even better still greater than 190 g, after a few days of casting, when it is subjected to penetration, to a depth of 10 mm, of a P20 spindle (prespeed of 1 mm/s, speed of 1 mm/s, trigger 10 g).

Fatty Phase

Fatty Alcohol

As mentioned previously, the composition according to the invention comprises from 4.0% to 8.0% by weight, relative to the total weight of the composition, of at least one fatty alcohol, For the purposes of the invention, the fatty alcohols are linear, and saturated or unsaturated, and comprise from 12 to 26 carbon atoms and preferably from 14 to 22 carbon atoms.

Preferably, for the purposes of the invention, the fatty alcohols are solid.

The fatty alcohol(s) that are suitable for use in the invention are preferably chosen from the group comprising cetyl alcohol, stearyl alcohol, cetylstearyl alcohol, myristyl alcohol, lauryl alcohol, tridecyl alcohol, pentadecyl alcohol, hexadecyl alcohol, arachidyl alcohol, behenyl alcohol and myricyl alcohol; they are preferably chosen from cetyl alcohol, stearyl alcohol and cetylstearyl alcohol.

As cetyl alcohols that may be most particularly suitable for use in the invention, use may be made, for example, of the products sold under the names Ecorol® 16/98 F and Ecorol® 16/98 P sold by the company Ecogreen Oleochemicals, Tegoalkanol® 16 sold by the company Evonik Goldschmidt, Lanette® 16 sold by the company Cognis, Vegarol® 1698 sold by the company VVF, Alkonat® 1698 P sold by the company Oxiteno, Cetyl Alcohol 98% Min sold by the company Emery Oleochemicals, Ginol® 16 (98%) sold by the company Godrej Industries, Nacol® 16-98 sold by the company Sasol, Kalcol® 6098 sold by the company Kao, and Acilol® 16 sold by the company Aegis Chemical.

As stearyl alcohols that are most particularly suitable for use in the invention, use may be made, for example, of those sold under the names Tegoalkanol® 18 sold by the company Evonik Goldschmidt, Ecorol® 18/98 F and Ecorol® 18/98 P sold by the company Ecogreen Oleochemicals, Lanette® 18 sold by the company Cognis, Kalcol® 8098 sold by the company Kao, Acilol® 18 sold by the company Aegis Chemical, Nacol® 18-98 sold by the company Sasol and NAA® 45 sold by the company Nihon Yushi.

As cetylstearyl alcohols that are most particularly suitable for use in the invention, use may be made, for example, of those sold under the names Ecorol® 68/50 F and Ecorol® 68/50 P sold by the company Ecogreen Oleochemicals, Lanette® O OR and Lanette® O OR Flakes sold by the company Cognis, Alkonat® 1618 C50 P sold by the company Oxiteno, Nafol® 16-18 EN sold by the company Sasol, Alcohol Cetoestearilico 50/50 sold by the company Industria Quimica Del Centro, Conol® 30 CK sold by the company New Japan Chemical, Cetylstearyl Alcohol 50:50 sold by the company Evonik Goldschmidt, Kalcol® 6850 sold by the company Kao, Vegarol® 1618 (50:50) sold by the company VVF and Ginol® 1618 50:50 OR sold by the company Godrej Industries.

According to one preferred embodiment, the composition according to the invention comprises a content of fatty alcohol(s) ranging from 4.0% to 6.0% by weight relative to the total weight of the composition.

Solid Linear Ester

The composition according to the invention comprises from 1.0% to 3.0% by weight, relative to the total weight of the composition, of at least one solid linear ester.

For the purposes of the invention, the solid linear esters contain from 25 to 36 carbon atoms and have melting points of between 38° C. and 60° C. A linear ester is said to the in be solid state when all of its mass is in solid crystalline form at room temperature.

The solid linear esters that are suitable for use in the invention are preferably chosen from the group comprising stearyl stearate, tetradecanoic acid or tetradecyl ester (INCI name: myristyl myristate), arachidyl propionate, cetyl myristate, stearyl myristate, myristyl palmitate, stearyl palmitate, myristyl stearate, cetyl stearate, stearyl stearate and cetyl palmitate, and mixtures thereof.

As stearyl stearate that is most particularly suitable for use in the invention, use may be made, for example, of the product sold under the name Liponate® SS sold by the company Lipo Chemicals.

As arachidyl propionate that is most particularly suitable for use in the invention, use may be made, for example, of the product sold under the name Waxenol® 801 sold by the company Alzo.

As examples of mixtures of solid linear esters that are most particularly suitable for the invention, mention may be made of myristyl/cetyl/stearyl myristate/palmitate/stearate (INCI name: cetyl esters (and) cetyl esters), for example sold under the names Crocamol® MS-PA-(MH), Crocamol® MS-PA-(BR), Crocamol® MS-PA-(SG) and Crocamol® MS-PA-(MV) sold by the company Croda, and Miraceti® sold by the company Laserson.

As cetyl palmitate that is most particularly suitable for use in the invention, use may be made, for example, of the product sold under the name Cutina® CP sold by the company Cognis.

The composition according to the invention preferably comprises tetradecanoic acid or tetradecyl ester.

This solid linear ester is especially sold under the name Tegosoft® MM by the company Evonik Goldschmidt.

According to one preferred embodiment, the composition according to the invention comprises a content of solid linear or ester(s) ranging from 1.0% to 2.0% by weight relative to the total weight of the composition.

Non-Ethoxylated Glyceryl Stearate

A composition according to the invention comprises from 2.5% to 6.0% by weight, relative to the total weight of the composition, of at least one non-ethoxylated glyceryl stearate.

The non-ethoxylated glyceryl stearates that are suitable for use in the invention are preferably chosen from the group comprising glyceryl mono-/di-/tri-stearate, glyceryl mono-/di-stearate and glyceryl mono-stearate.

According to one variant, the non-ethoxylated glyceryl stearates that are suitable for use in the invention are preferably chosen from the group constituted by glyceryl mono-/di-/tri-stearate, glyceryl mono-/di-stearate and glyceryl mono-stearate.

As glyceryl mono-/di-/tri-stearate that is most particularly suitable for use in the invention, use may be made, for example, of the product sold under the name Dub® GMS sold by the company Stéarineries Dubois.

As glyceryl mono-/di-stearate that is most particularly suitable for use in the invention, use may be made, for example, of the products sold under the names Cerasynt® SD sold by the company ISP, Geleol® Pastilles L'Oréal sold by the company Gattefosse and Dub® GMS 50/50 sold by the company Stéarineries Dubois.

The composition according to the invention comprises at least one non-ethoxylated glyceryl stearate, preferably glyceryl mono-stearate, sold especially under the name Cutina® GMS V sold by the company Cognis.

According to one preferred embodiment, the composition according to the invention comprises a content of non-ethoxylated glyceryl stearate(s) ranging from 2.5% to 4.0% by weight relative to the total weight of the composition.

Sodium Polyacrylate

A composition according to the invention comprises from 0.25% to 0.50% by weight, relative to the total weight of the composition, of sodium polyacrylate.

Sodium polyacrylates are acrylic homopolymers in partially or totally neutralized form.

According to one particular mode, they are hydrophilic.

According to the invention, the term "hydrophilic polymer" means a non-amphiphilic polymer that is soluble and dispersible in water.

The sodium polyacrylates may be present in the composition in a particulate or non-particulate form.

When they are present in a particulate form, their mean size in the hydrated state is preferably less than or equal to 10 µm and even more preferentially less than or equal to 5 µm. Their mean size in the non-hydrated state is preferably less than or equal to 2 µm, preferably less than or equal to 1 µm.

As regards these acrylic polymers already neutralized before use, or otherwise, examples that may be mentioned include:
  sodium polyacrylates such as those sold under the name Cosmedia SP® containing 90% solids and 10% water, or Cosmedia SPL® as an inverse emulsion containing about 60% dry active material, an oil (hydrogenated polydecene) and a surfactant (PPG-5 laureth-5), both sold by the company Cognis;
  partially neutralized sodium polyacrylates that are in the form of an inverse emulsion comprising at least one polar oil, for example the product sold under the name Luvigel® EM sold by the company BASF, and mixtures thereof.

An acrylic acid polymer which has not been neutralized beforehand, may be neutralized by any suitable means and especially by adding sodium hydroxide. Sodium polyacrylates are thus obtained.

The neutralization may be performed prior to use in the composition of the invention if the polymer in question is sold in a non-neutralized form. On the other hand, for some of them, neutralization is inherent to the starting material. This is the case especially for Luvigel® EM and for the products named Cosmedia® SP and SPL, which are already partially neutralized.

The neutralization step with sodium counterions, is important for giving the acidic polymers their gelling properties and thus stabilization of the composition. The said acrylic polymers are converted into the corresponding acrylate polymers during this neutralization step. The said acrylic monomers of the acrylic polymer according to the invention may be neutralized to a proportion of from 5% to 80%.

The acrylic polymer(s) in accordance with the invention do not comprise any monomer other than partially or totally neutralized acrylic acid.

According to one particular embodiment, the acrylic acid homopolymer may be in the form of a water-in-oil emulsion, known as an inverse emulsion. This inverse emulsion may be obtained, for example, by inverse emulsion polymerization.

According to one particular embodiment of the invention, the polymer used is a partially neutralized sodium polyacrylate that is in the form of an inverse emulsion comprising at least one polar oil. Among the oils, mention may be made of fatty acid esters. Examples of these fatty acid esters are isopropyl esters of fatty acids, such as isopropyl palmitate or isopropyl myristate, or fatty acid polyglycerides, in particular of fatty acid mixtures comprising at least 50% of capric and/or caprylic acid. Such water-in-oil emulsions are described in document U.S. Pat. No. 6,197,283.

According to this embodiment, the oily phase may be constituted by one or more fatty acid esters, one or more fatty acid polyglycerides based on a mixture of polyglycerides, which contains diglycerides and triglycerides, with mixtures of fatty acids, which contain caprylic acid and/or capric acid, preferably in a proportion of at least 50% by weight relative to the total weight of fatty acids.

According to one embodiment of the invention, the oil content of the inverse emulsion is between 15% and 70% by weight and in particular between 20% and 35% by weight relative to the total weight of the inverse emulsion.

In this respect, mention may be made especially of Luvigel® EM, the oily phase of which comprises 26% of oil phase constituted by $C_8$-$C_{10}$ triglycerides, that is to say the fatty acids which are a mixture of caprylic and capric acid.

Moreover, the water-in-oil emulsion may contain from 0.25% to 7% by weight and preferably 0.5% to 5% by weight of a surfactant.

The at least partially neutralized acrylic polymer may be present in the inverse emulsion in a content ranging from 20% to 70% by weight, in particular from 20% to 65% by weight, for example from 20% to 62% by weight relative to the total weight of the inverse emulsion.

In particular, according to one embodiment, the at least partially neutralized acrylic polymer may be present in the inverse emulsion in a content ranging from 20% to 30% by weight relative to the total weight of the inverse emulsion. According to yet another embodiment, the at least partially neutralized acrylic polymer may be present in the inverse emulsion in a content ranging from 50% to 62% by weight relative to the total weight of the composition.

In the water-in-oil formulation of such a polymer, the oily phase may then be constituted by one or more fatty acid esters as described previously.

The at least partially neutralized homopolymer(s) may or may not be crosslinked.

When they are crosslinked, the crosslinking of the acrylic acid may be obtained according to any method known to those skilled in the art, especially according to the description of document U.S. Pat. No. 6,197,283 or according to the description of document U.S. Pat. No. 6,444,785, which mention the crosslinking agents that may be used.

Among these, mention may be made of unsaturated compounds that are soluble in water or in oil. Such crosslinking agents are especially methylenebisacrylamide, divinylpyrrolidone, alkyl (meth)acrylate, triallylamine, ethylene glycol diacrylates (up to 50 EO), (meth)acrylic esters with di- or polyhydric alcohols such as trimethylolpropane triacrylate or pentaerythrityl tetraacrylate.

According to one embodiment, the crosslinking agent is water-soluble.

According to another embodiment, the crosslinking agent is triallylamine.

The preparation of W/O emulsions comprising a polymer in accordance with the present invention may be performed according to the teaching of document U.S. Pat. No. 6,444,785. The object of this process is to lower the content of remaining monomers by post-treatment with a redox initiator system. According to this process, the post-treatment of the W/O emulsion is performed by addition of a redox initiator system which comprises essentially
a) 0.001% to 5% by weight, relative to the total amount of monomers used for the preparation of the polymer,
a1) of an oxidizing agent $R^1OOH$,
in which $R^1$ denotes hydrogen, a $C_1$ to $C_8$ alkyl group or a $C_6$ to $C_{12}$ aryl group, and/or
a2) of a compound that releases hydrogen peroxide in aqueous medium, and
b) 0.005% to 5% by weight, relative to the total amount of monomers used for the preparation of the polymer,
b1) of an α-hydroxycarbonyl compound having the following formula:

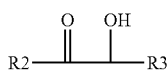

in which the groups have, independently of each other, the following meaning:
R2 hydrogen, a $C_1$-$C_{12}$ alkyl group, optionally containing functional groups and/or possibly comprising olefinic unsaturations,
$R^3$ hydrogen, OH, a $C_1$-$C_{12}$ alkyl group, optionally containing functional groups and/or possibly comprising olefinic unsaturations,
and whereas $R_2$ and $R_3$ may form a cyclic structure, which may contain a heteroatom and/or functional groups, and/or may comprise olefinic unsaturations, and/or
b2) of a compound that releases such an α-hydroxycarbonyl compound in aqueous medium, and
c) catalytic amounts of a multivalent metal ion that may be present in several valency states.

As sodium polyacrylate that is most particularly suitable for use in the invention, use may be made, for example, of the product sold under the name Cosmedia® SP sold by the company Cognis.

According to one preferred embodiment, the composition according to the invention comprises a content of sodium polyacrylate ranging from 0.25% to 0.30% by weight relative to the total weight of the composition.

Oil

According to one advantageous embodiment, the fatty phase of the composition according to the invention comprises at least one oil.

The oil(s) may be chosen from volatile oils and/or non-volatile oils, or mixtures thereof.

The term "oil" means a water-immiscible non-aqueous compound that is liquid at room temperature (25° C.) and at atmospheric pressure (760 mmHg).

Volatile Oils

For the purposes of the present invention, the term "volatile oil" means an oil (or non-aqueous medium) capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferably ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity≤8 centistokes ($8 \times 10^{-6}$ $m^2/s$), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

Non-Volatile Oil

Preferably, the composition according to the invention comprises at least one non-volatile oil.

The term "non-volatile" refers to an oil whose vapour pressure at room temperature and atmospheric pressure is non-zero and less than 0.02 mmHg (2.66 Pa) and better still less than $10^{-3}$ mmHg (0.13 Pa).

The non-volatile oils may be hydrocarbon-based oils especially plant origin, oils of synthetic or mineral origin, silicone oils or fluoro oils, or mixtures thereof.

Apolar Oil

According to a first embodiment, the said non-volatile oil may be an apolar oil, which is preferably hydrocarbon-based.

These oils may be of plant, mineral or synthetic origin.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the article by C. M. Hansen: *The three dimensional solubility parameters*, J. Paint Technol. 39, 105 (1967).

According to this Hansen space:
$\delta_D$ characterizes the London dispersion forces derived from the formation of dipoles induced during molecular impacts;
$\delta_p$ characterizes the Debye interaction forces between permanent dipoles and also the Keesom interaction forces between induced dipoles and permanent dipoles;
$\delta_h$ characterizes the specific interaction forces (such as hydrogen bonding, acid/base, donor/acceptor, etc.); and
$\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

Preferably, the non-volatile apolar hydrocarbon-based oil may be chosen from linear or branched hydrocarbons of mineral or synthetic origin, such as:
liquid paraffin or derivatives thereof,
squalane,
soeicosane,
naphthalene oil,
polybutylenes such as Indopol H-100 (molar mass or MW=965 g/mol), Indopol H-300 (MW=1340 g/mol) and Indopol H-1500 (MW=2160 g/mol) sold or manufactured by the company Amoco,
hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, and mixtures thereof.

Polar Oil

According to one particular embodiment, the fatty phase also comprises at least one polar oil.

For the purposes of the present invention, the term "polar oil" means an oil whose solubility parameter at 25° C., $\delta_a$, is other than 0 $(J/cm^3)^{1/2}$.

The polar oil may be a hydrocarbon-based, silicone and/or fluoro oil.

These oils may be of plant, mineral or synthetic origin.

The term "polar hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The term "silicone oil" means an oil containing at least one silicon atom, and especially containing Si—O groups.

The term "fluoro oil" means an oil containing at least one fluorine atom.

In particular, the non-volatile polar oil may be chosen from the list of oils below, and mixtures thereof:

hydrocarbon-based polar oils such as phytostearyl esters, such as phytostearyl oleate, phytostearyl isostearate and lauroyl/octyldodecyl/phytostearyl glutamate (Ajinomoto, Eldew PS203), triglycerides consisting of fatty acid esters of glycerol, in particular the fatty acids of which may have chain lengths ranging from $C_4$ to $C_{36}$, and especially from $C_{18}$ to $C_{36}$, these oils possibly being linear or branched, and saturated or unsaturated; these oils may especially be heptanoic or octanoic triglycerides, wheatgerm oil, sunflower oil, grapeseed oil, sesame seed oil (820.6 g/mol), corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil or musk rose oil; shea butter; or alternatively caprylic/capric acid triglycerides, for instance those sold by the company STEARINERIES DUBOIS or those sold under the names MIGLYOL 810®, 812® and 818® by the company Dynamit Nobel;

synthetic ethers containing from 10 to 40 carbon atoms, such as dicaprylyl ether;

hydrocarbon-based esters of formula RCOOR' in which RCOO represents a carboxylic acid residue comprising from 2 to 40 carbon atoms, and R' represents a hydrocarbon-based chain containing from 1 to 40 carbon atoms, such as cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethyl hexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate and 2-octyldodecyl neopentanoate, isononanoic acid esters, for instance isononyl isononanoate, isotridecyl isononanoate and octyl isononanoate, oleyl erucate, isopropyl lauroyl sarcosinate, diisopropyl sebacate, isocetyl stearate, isodecyl neopentanoate, isostearyl behenate, and myristyl myristate;

polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast® 14436H (INCI name: dilinoleic acid/butanediol copolymer), or else copolymers of polyols and of dimer diacids, and esters thereof, such as Hailuscent® ISDA;

polyol esters and pentaerythritol esters, for instance dipentaerythrityl tetrahydroxystearate/tetraisostearate;

$C_{12}$-$C_{22}$ higher fatty acids, such as oleic acid, linoleic acid and linolenic acid, and mixtures thereof;

fluorinated oils which are optionally partially hydrocarbon-based and/or silicone-based;

silicone oils such as phenyl silicones, for instance Belsil® PDM 1000 from the company Wacker (MW=9000 g/mol), fatty acids containing from 12 to 26 carbon atoms, for instance oleic acid;

dialkyl carbonates, the two alkyl chains possibly being identical or different, such as dicaprylyl carbonate sold under the name CETIOL CC® by Cognis; and non-volatile oils of high molecular mass, for example between 400 and 10 000 g/mol, in particular between 650 and 10 000 g/mol, for instance:

i) vinylpyrrolidone copolymers such as the vinylpyrrolidone/1-hexadecene copolymer, Antaron V-216 sold or manufactured by the company ISP (MW=7300 g/mol);

ii) esters such as:

a) linear fatty acid esters with a total carbon number ranging from 35 to 70, for instance pentaerythrityl tetrapelargonate (MW=697.05 g/mol);

b) hydroxylated esters such as polyglycerol-2 triisostearate (MW=965.58 g/mol);

c) aromatic esters such as tridecyl trimellitate (MW=757.19 g/mol), $C_{12}$-$C_{15}$ alcohol benzoate, the 2-phenylethyl ester of benzoic acid, and butyloctyl salicylate;

d) esters of $C_{24}$-$C_{28}$ branched fatty acids or fatty alcohols such as those described in patent application EP-A-0 955 039, and especially triisoarachidyl citrate (MW=1033.76 g/mol), pentaerythrityl tetraisononanoate (MW=697.05 g/mol), glyceryl triisostearate (MW=891.51 g/mol), glyceryl tris(2-decyl)tetradecanoate (MW=1143.98 g/mol), pentaerythrityl tetraisostearate (MW=1202.02 g/mol), polyglyceryl-2 tetraisostearate (MW=1232.04 g/mol) or else pentaerythrityl tetrakis(2-decyl)tetradecanoate (MW=1538.66 g/mol), e) esters and polyesters of dimer diol and of monocarboxylic or dicarboxylic acid, such as esters of dimer diol and of fatty acid and esters of dimer diol and of dimer dicarboxylic acid, such as Lusplan DD-DA5® and Lusplan DD-DA7® sold by the company Nippon Fine Chemical and described in patent application US 2004-175 338, the content of which is incorporated into the present application by reference;

and mixtures thereof.

Preferably, the polar oil is chosen from the hydrocarbon-based esters of formula RCOOR' in which RCOO represents a carboxylic acid residue containing from 2 to 40 carbon atoms, and R' represents a hydrocarbon-based chain containing from 1 to 40 carbon atoms.

Preferably, the polar oil is isopropyl myristate.

According to another variant, the fatty phase is also constituted by at least one polar oil, preferably chosen from the hydrocarbon-based esters of formula RCOOR' in which RCOO represents a carboxylic acid residue comprising from 2 to 40 carbon atoms and R' represents a hydrocarbon-based chain containing from 1 to 40 carbon atoms, and more particularly isopropyl myristate.

Vegetable Butters

According to another variant, the fatty phase may comprise vegetable butters.

The vegetable butters that are suitable for use in the invention are preferably chosen from the group comprising avocado butter, cocoa butter, shea butter, kokum butter, mango butter, murumuru butter, coconut butter, apricot kernel butter, sal butter and urukum butter, and mixtures thereof.

The fatty phase preferably comprises less than 10% of vegetable butters, or even less than 7% of vegetable butters, and advantageously the fatty phase is free of vegetable butters.

Advantageously, the composition according to the invention comprises a fatty phase in a content of between 10% and 70% and preferably between 15% and 40% by weight relative to the total weight of the composition.

Aqueous Phase

As indicated previously, a composition according to the invention comprises an aqueous phase.

The aqueous phase comprises water. A water that is suitable for use in the invention may be a floral water such as cornflower water and/or a mineral water such as Vittel water, Lucas water or La Roche Posay water and/or a demineralized water.

The aqueous phase may also comprise water-miscible organic solvents (at room temperature: 25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

The aqueous phase may also comprise any water-soluble or water-dispersible compound that is compatible with an aqueous phase, such as gelling agents, film-forming polymers, thickeners or surfactants, and mixtures thereof.

According to one advantageous embodiment, the composition of the invention may comprise an aqueous phase in a content ranging from 30% to 90% by weight and more particularly from 60% to 85% by weight relative to the total weight of the composition.

Additives

A composition of the invention may also comprise any additive usually used in the field under consideration, other than the components of the composition defined above, chosen, for example, from surfactants and co-surfactants, pasty compounds, gums, plasticizers, gelling agents, thickeners, antioxidants, pigments, water-soluble or liposoluble dyes, polymeric or non-polymeric film-forming agents, cosmetic active agents, UV-screening agents, emollients, moisturizers, trace elements, softeners, sequestrants, vitamins, preserving agents, fragrances, neutralizers, antiseptics and anti-ageing active agents, and mixtures thereof.

It is a matter of routine operations for a person skilled in the art to adjust the nature and amount of the additives present in the compositions in accordance with the invention such that the desired cosmetic properties thereof are not thereby affected.

Such compositions are especially prepared according to the general knowledge of a person skilled in the art.

Throughout the description, including the claims, the term "comprising a" should be understood as being synonymous with "comprising at least one", unless otherwise mentioned.

The terms "between . . . and . . . " and "ranging from . . . to . . . " should be understood as being inclusive of the limits, unless otherwise specified.

The composition according to the invention may be a skin makeup and/or care composition, and may constitute a face powder, an eyeshadow, a lipstick, a face product, a foundation, a concealer product, a body makeup product, a facial or body care product, an antisun product or a haircare product, especially a hair mask.

The composition according to the invention is advantageously stored in a jar, a box or a case, equipped with a closing member in the form of a removable stopper, a lid, a cap, a tear-off strip or a capsule, especially of the type comprising a body fixed to the container and a cover articulated on the body.

The examples that follow are presented as non-limiting illustrations of the invention. Unless otherwise mentioned, the amounts indicated are expressed as mass percentages.

Example: Composition According to the Invention

A composition was prepared from fatty alcohols, solid linear esters, glyceryl stearate and sodium polyacrylate according to the following procedure.

The fatty phase comprising a mixture of 5.0% by weight of fatty alcohol, 1.2% by weight of a solid linear ester, 4.0% by weight of at least one non-ethoxylated glyceryl stearate, and oils, is heated to 70° C.

The fatty phase is added to the aqueous phase, which is at room temperature. The mixture is prepared at a temperature of 65° C.

The sodium polyacrylate is added with stirring using a turbomixer.

The turbomixer stirring is continued down to the crystallization temperature of the mixture, 41° C.

The composition is cast in a conditioning jar at 40° C.

The composition is left to stand at room temperature for one month.

The table below reports the composition of the prepared formulation.

| Compounds | Composition according to the invention (mass %) |
|---|---|
| PEG-100 Stearate | 0.7 |
| Glyceryl stearate sold under the name Cutina ® GMS V by the company Cognis | 4.0 |

-continued

| Compounds | Composition according to the invention (mass %) |
|---|---|
| Cetylstearyl alcohol sold under the name Lanette ® O OR by the company Cognis (fatty alcohol) | 5 |
| Myristyl myristate sold under the name Tegosoft ® MM by the company Evonik Goldschmidt (solid linear ester) | 1.2 |
| Glycerol | 10 |
| Dimethicone | 2.5 |
| Sodium polyacrylate | 0.28 |
| Mixture of apricot oil sold under the name Lipovol ® by the company Lipo Chemicals and of shea butter sold under the name Lipex ® 102 by the company Aarhuskarlshamn in a ratio (0.8% + 0.5%) | 1.3 |
| Isopropyl palmitate sold by the company Cognis | 5 |
| Phenoxyethanol | 0.8 |
| Benzoic acid | 0.1 |
| Water | qs 100 |

The texture obtained is thick, smooth, non-tacky, sparingly film-forming and sparingly greasy.

The composition does not flow under its own weight.

The composition penetrates rapidly, and the formula is creamy on application.

The deposit formed by this composition does have a greasy and tacky feel.

When it is taken up and used, it affords a pleasant sensory experience.

The invention claimed is:

1. A cosmetic composition, comprising, in a physiologically acceptable medium and relative to a total weight of the composition:
    from 4.0% to 8.0% by weight of at least one fatty alcohol,
    from 1.0% to 3.0% by weight of at least one solid linear ester selected from the group consisting of stearyl stearate, myristyl myristate, arachidyl propionate, cetyl myristate, stearyl myristate, myristyl palmitate, stearyl palmitate, myristyl stearate, cetyl stearate, and cetyl palmitate,
    from 2.5% to 6.0% by weight of at least one non-ethoxylated glyceryl stearate,
    from 0.25% to 0.50% by weight of sodium polyacrylate, and
    at least one vegetable butter in a content of from greater than 0 to less than 7% by weight,
    wherein the composition is suitable for making up or caring for a keratin material and is an oil-in-water solid emulsion.

2. The composition according to claim 1, further comprising: an aqueous phase of from 30% to 90% by weight relative to the total weight of the composition.

3. The composition according to claim 1, wherein the at least one fatty alcohol is selected from the group consisting of cetyl alcohol, stearyl alcohol and cetylstearyl alcohol.

4. The composition according to claim 1, wherein the at least one non-ethoxylated glyceryl stearate is selected from the group consisting of monostearate, glyceryl distearate, and glyceryl tristearate.

5. The composition according to claim 1, wherein the composition has, at a temperature of 20° C., a hardness of greater than or equal to 100 g.

6. The composition according to claim 1, wherein the composition has, at a temperature of 20° C., a viscosity of between 95 and 220 poises at t=0, between 65 and 200 at t=30 seconds and between 30 and 150 at t=10 minutes.

7. The composition according to claim 1, further comprising:
    at least one additive selected from the group consisting of a surfactant, a co-surfactant, a pasty compound, a gum, a plasticizer, a gelling agent, a thickener, an antioxidant, a pigment, a water-soluble or liposoluble dye, a polymeric or non-polymeric film-forming agent, a cosmetic active agent, a UV-screening agent, an emollient, a moisturizer, a trace element, a softener, a sequestrant, a vitamin, a preserving agent, a fragrance, a neutralizer, an antiseptic, and an anti-ageing active agent.

8. The cosmetic composition according to claim 1, wherein the composition is a foundation composition.

9. The composition according to claim 1, further comprising: an aqueous phase of from 60% to 85% by weight relative to the total weight of the composition.

10. The composition according to claim 1, wherein the composition has, at a temperature of 20° C., a hardness of greater than or equal to 160 g.

11. The composition according to claim 1, wherein the composition has, at a temperature of 20° C., a hardness of greater than 190 g.

12. The composition according to claim 1, wherein the composition is free of UV-screening agent.

13. A process for preparing the composition according to claim 1, the process comprising:
    obtaining a fatty phase comprising a first mixture of 4.0% to 8.0% by weight of the at least one fatty alcohol, 1.0% to 3.0% by weight of the at least one solid linear ester selected from the group consisting of stearyl stearate, myristyl myristate, arachidyl propionate, cetyl myristate, stearyl myristate, myristyl palmitate, stearyl palmitate, myristyl stearate, cetyl stearate, and cetyl palmitate, 2.5% to 6.0% by weight of the at least one non-ethoxylated glyceryl stearate, at least one vegetable butter in a content of from greater than 0 to less than 7% by weight, and optionally an oil,
    adding the fatty phase to an aqueous phase at a minimum temperature of 65° C., thereby obtaining a second mixture,
    reducing temperature of the second mixture to a temperature of between 60 and 65° C.,
    adding 0.25% to 0.50% by weight of sodium polyacrylate to the second mixture, thereby obtaining a third mixture,
    stirring the third mixture, optionally with a turbomixer, down to crystallization temperature of the third mixture, thereby obtaining a composition,
    pouring the composition into a conditioning jar at the crystallization temperature, thereby obtaining a conditioned composition as an oil-in-water solid emulsion, and
    optionally leaving the conditioned composition to stand for one month at room temperature.

14. A cosmetic process for making up or caring for a keratin material, the process comprising: applying the composition according to claim 1 to a keratin material in need thereof.

15. The cosmetic process according to claim 14, wherein the cosmetic process is suitable for moisturizing skin.

* * * * *